(12) United States Patent
Heath et al.

(10) Patent No.: US 7,276,043 B2
(45) Date of Patent: Oct. 2, 2007

(54) OCCLUSION-RESISTANT CATHETER

(75) Inventors: Kevin R. Heath, Weston, MA (US); Michelle M. Berry, Franklin, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 331 days.

(21) Appl. No.: 10/059,925

(22) Filed: Jan. 29, 2002

(65) Prior Publication Data

US 2003/0144623 A1 Jul. 31, 2003

(51) Int. Cl.
A61M 37/00 (2006.01)
A61M 25/00 (2006.01)
A61M 3/00 (2006.01)

(52) U.S. Cl. .................. 604/6.16; 604/43; 604/523

(58) Field of Classification Search .............. 604/6.16, 604/7–10, 523, 524, 508, 93.01, 264, 526, 604/527, 532, 544; 600/435; 606/153; 138/115, 138/118
See application file for complete search history.

(56) References Cited

U.S. PATENT DOCUMENTS

| | | | |
|---|---|---|---|
| 4,134,402 A | | 1/1979 | Mahurkar |
| 4,661,094 A | | 4/1987 | Simpson |
| 4,681,570 A | * | 7/1987 | Dalton .................... 604/524 |
| 4,694,838 A | * | 9/1987 | Wijayarthna et al. ....... 600/435 |
| 4,795,439 A | * | 1/1989 | Guest ...................... 604/43 |
| 4,813,925 A | * | 3/1989 | Anderson et al. ............. 604/8 |
| 4,850,969 A | | 7/1989 | Jackson |
| 4,995,865 A | | 2/1991 | Gahara et al. |
| 5,190,520 A | * | 3/1993 | Fenton et al. ................ 604/43 |
| 5,201,723 A | | 4/1993 | Quinn |
| 5,509,897 A | * | 4/1996 | Twardowski et al. ......... 604/43 |
| 5,554,114 A | | 9/1996 | Wallace et al. |
| 5,873,865 A | | 2/1999 | Horzewski et al. |
| 6,117,106 A | | 9/2000 | Wasicek et al. |
| 6,193,685 B1 | | 2/2001 | Goodin |

FOREIGN PATENT DOCUMENTS

EP   0 386 408 A1   9/1990

OTHER PUBLICATIONS

International Search Report for corresponding PCT application No. PCT/US03/02603, mailed Jun. 27, 2003.

* cited by examiner

Primary Examiner—Tatyana Zalukaeva
Assistant Examiner—Leslie R. Deak
(74) Attorney, Agent, or Firm—RatnerPrestia

(57) ABSTRACT

A catheter comprises an elongated tube having an interior defined by a sidewall having openings. At least a portion of the catheter is spirally formed into a corkscrew pattern or has an inwardly spiraling portion with at least one opening coincident therewith. Additionally or alternatively, the catheter comprises a septum that divides the interior into at least first and second lumens. The first and second lumens may form a double helix in a portion of the catheter coincident with the plurality of openings or along the entire length of the catheter. Methods of manufacturing the catheters involve extruding the portion of the catheter having the openings, making this portion separately then attaching it to another catheter, or heating and deforming a portion of a catheter to form a tip portion. The catheter can be used for hemodialysis by drawing blood through one lumen and returning it through another.

24 Claims, 3 Drawing Sheets

OCCLUSION-RESISTANT CATHETER

TECHNICAL FIELD

This invention relates generally to perfusion catheters and, more specifically, to a catheter that is resistant to occlusion of its sidewall openings.

BACKGROUND OF THE INVENTION

Perfusion catheters used for introducing or removing fluids from a body lumen are well known in the art. Such catheters may be used in drug therapy, such as chemotherapy, where the fluid to be introduced is a pharmaceutical agent. Perfusion catheters have also been used to allow for bypassing occlusions in blood vessels. For example, during angioplasty, plaque may become partially or completely dislodged and may form a restriction that at least partially occludes an arterial passage. A perfusion catheter may be positioned in the occluded blood vessel across the restriction, such as is described in U.S. Pat. No. 4,661,094, incorporated herein by reference, to allow blood to flow into the catheter through a first opening upstream of the restriction and flow out through a second opening downstream of the restriction. As described in the '094 patent, the openings may be distributed in a helical pattern in the sidewalls of the catheter.

During the intake of fluids, however, the sidewall hole orientation may have certain disadvantages. For example, the holes may contact and seal against the walls of the duct or vessel in which the catheter resides, thereby blocking the holes and minimizing flow. One typical use for perfusion catheters for fluid intake is in extracorporeal blood purification procedures, such as hemodialysis. Modern procedures favor the use of dual-lumen catheters such as those described in U.S. Pat. No. 4,134,402, incorporated herein by reference, or other multi-lumen catheters, such as those described in U.S. Pat. No. 4,995,865, incorporated herein by reference. In a standard dialysis procedure using a dual- or multi-lumen catheter, blood is withdrawn from a blood vessel in a patient through one or more lumens of the multi-lumen catheter and supplied to a hemodialysis unit that purifies the blood. The purified blood is then returned to the patient through another lumen of the catheter.

The '865 patent describes multi-lumen catheters having side openings located on "spiral pathways." The ranges of these spiral pathways, however, are limited to the portions of spirals contained within two pie-shaped intake lumens that each comprise only a 90° quadrant of the circular lumen. Thus, if there is a tendency for one circumferential portion of the catheter to be blocked and that portion happens to fall within one or both of the quadrants comprising the two intake lumens, the spiral configuration is insufficient to keep the flow into the openings from becoming occluded. Occlusion of intake holes may reduce the intake flow significantly enough to lengthen the amount of time a patient may have to undergo the hemodialysis procedure, causing unnecessary discomfort for the patient, and causing inefficient use of resources for the dialysis provider.

Therefore, there is still a need in the art for a catheter structure that resists occlusion of openings in the sidewall.

SUMMARY OF THE INVENTION

It is to be understood that both the foregoing general description and the following detailed description are exemplary, but not restrictive, of the invention.

One aspect of the invention is a catheter comprising an elongated tube having an interior defined by a sidewall having a plurality of openings in the sidewall. At least a portion of the catheter is spirally formed into a corkscrew pattern to define a corkscrew-patterned portion. One or more of the openings is coincident with the corkscrew-patterned portion. The corkscrew pattern comprises an outer diameter and an inner diameter, and the plurality of openings faces the inner diameter in one embodiment. In another embodiment, the catheter may comprise a septum that divides the interior into at least a first lumen and a second lumen. The first lumen and the second lumen may form a double helix in a portion of the catheter coincident with the plurality of openings or along the entire length of the catheter. The septum may divide the interior into more than two lumens that form a multiple helix, and the multiple lumens may form a multiple helix along the portion of the catheter coincident with the plurality of openings or along the entire length of the catheter.

According to another aspect of the invention, a catheter comprises an elongated tube having an interior defined by a sidewall having a plurality of openings, and a septum that divides the interior into at least a first lumen and a second lumen, wherein the first lumen and the second lumen form a double helix at least in a portion of the catheter coincident with the plurality of openings. In one embodiment, the double helix may run along the entire length of the catheter. In another embodiment, the septum may divide the interior into more than two lumens that form a multiple helix in a portion of the catheter adjacent the plurality of openings or along the entire length of the catheter.

Other aspects of the invention comprise methods for making catheters. One method comprises forming the multi-lumen catheter body; molding the catheter tip into the multi-helix, the corkscrew pattern, or both; and attaching the catheter body to the catheter tip. Another method comprises forming the multi-lumen catheter; heating at least the catheter tip of the multi-lumen catheter to a sufficient temperature at which the catheter tip can be deformed; deforming the catheter tip into the multi-helix, the corkscrew pattern, or both; and cooling the catheter tip. For a catheter of this invention with the twisting septum dividing an interior of the catheter into multiple lumens in a multi-helix, one method comprises extruding the catheter using an extrusion tooling insert that rotates to form the twisting septum. Another method comprises extruding the catheter and septum without a twist in the septum and then twisting the catheter as it exits the extruder.

Yet another aspect of the invention is a method for providing hemodialysis comprising the steps of introducing a multi-lumen catheter of this invention into a body lumen, taking in blood through the plurality of openings into a first catheter lumen; cleansing the blood by hemodialysis; and returning the blood through the second catheter lumen into the body lumen. The twisting septum, corkscrew pattern, or combination thereof in the multi-lumen catheter minimizes occlusion of the openings by the body lumen wall. Specifically, the method may comprise deploying the catheter with its distal end in or adjacent to the right atrium of the patient's heart. Where the catheter embodiment comprises a catheter tip with a corkscrew pattern and the second lumen extending distally further than a distal end of the first lumen and pointed in a direction toward the right atrium, the method may comprise returning the blood to the body lumen in a stream directed toward the right atrium.

Still another aspect of the invention comprises a catheter for deployment in a lumen having a wall, the catheter comprising an elongated tube comprising a catheter tip, one or more openings in the catheter tip, and a deformation in the catheter tip for preventing the one or more openings from contacting the lumen wall. In one embodiment, the deformation may be a corkscrew pattern, while in another embodiment the deformation may be an inwardly spiraling portion. The inwardly spiraling portion typically comprises an inner periphery that defines an open area, with sidewall openings facing into the open area and/or a distal end opening positioned within the open area.

BRIEF DESCRIPTION OF THE DRAWING

The invention is best understood from the following detailed description when read in connection with the accompanying drawing, in which.

DETAILED DESCRIPTION OF THE INVENTION

The invention will next be illustrated with reference to the figures wherein the same numbers indicate similar elements in all figures. Such figures are intended to be illustrative rather than limiting and are included herewith to facilitate the explanation of the apparatus of the present invention.

Figure 1A:
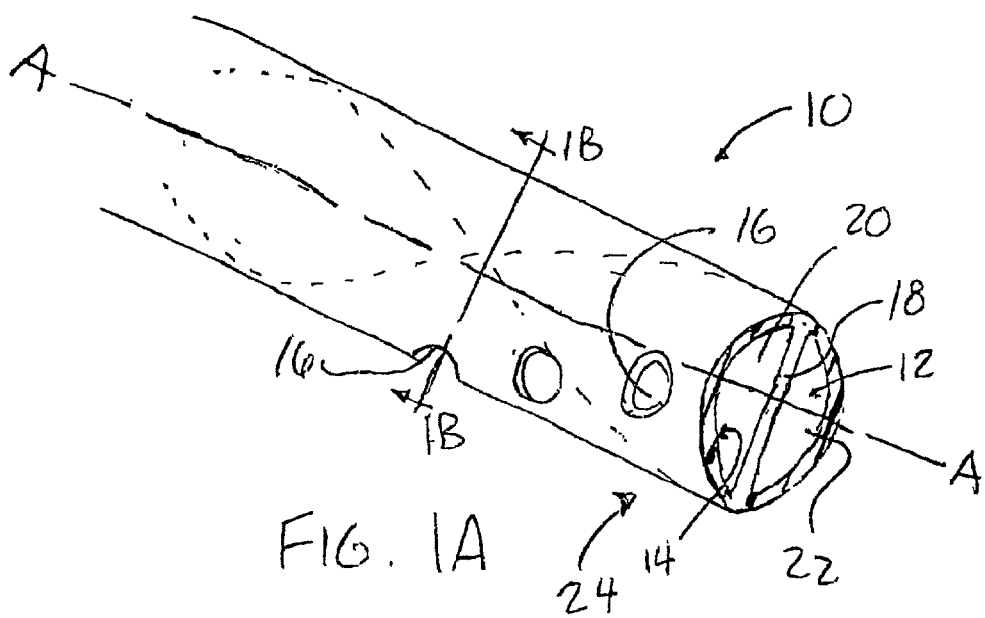
FIG. 1A shows a perspective view of an exemplary double-lumen catheter of the present invention in partial cross-section.

Referring now to FIGS. 1A-5, there are shown several embodiments of the invention. As shown in FIGS. 1A and 1B, catheter 10 comprises an elongated tube having an interior 12 defined by a sidewall 14 having a plurality of openings 16 formed in the sidewall, and a septum 18. Septum 18 divides interior 12 into a first lumen 20 and a second lumen 22. As shown by the dashed lines in FIG. 1A, the first lumen and second lumen form a double helix about one another as septum 18 twists about the common axis A of the catheter, as further illustrated by the cross section of FIG. 1B. FIG. 1B, a cross-section of catheter 10 taken a predetermined distance from the end 24 of the catheter shown in FIG. 1A, shows how septum 18, first lumen 20, and second lumen 22 are twisted 90° from their relationship as shown in FIG. 1A. Openings 16, which follow the path of the corresponding lumen 20 or 22, are therefore also in a helical pattern about axis A.

Figure 1B:
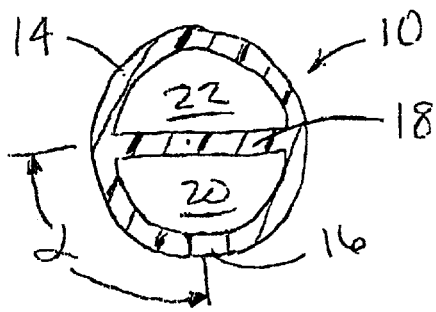
FIG. 1B shows a cross-sectional illustration of the catheter of FIG. 1A taken across line 1B-1B.

For a double-lumen catheter as shown in FIG. 1A, openings 16 may be aligned (using the central axis of the opening) at an angle α to the plane formed by septum 18, as shown in FIG. 1B. Openings may be distributed in a line so that angle α is 90° for all the openings as shown in FIG. 1B. In an alternative embodiment, the openings may be placed in two lines following the path of the lumen, one line at 60° and another line at 120°, including a pattern where the openings alternate between the two lines along the length of the catheter tip. One advantage of the multi-helical configuration, however, is that the simple 90° hole orientation may be used because the multi-helix prevents occlusion of multiple holes, so there is no need to offset the holes from one another relative to the septum. The catheters of this invention, however, are not limited to any particular hole pattern or distribution.

The degree of twist of per unit length of catheter 10 may have any value necessary to produce a desired effect. For example, for catheters having a diameter of 6-14 french (approximately 0.203-0.474 centimeters), a 360° twist may occur every 3-20 centimeters. Catheters of this invention, however, are not limited to any particular degree of twist.

The twisted septum 18 and resulting double helix pattern of first lumen 20 and second lumen 22 may extend along the entire length of the catheter for ease of manufacture, or may extend only in a portion of the catheter in which the openings are present. Stated another way, the first lumen 20 and the second lumen 22 form the double helix at least in a portion of the catheter 10 coincident with (i.e., occupying the same space as) the plurality of openings. The twisting relationship of the septum provides each lumen 20 and 22 of catheter 10 with an ever-changing relationship with the sidewall of a body lumen in which the catheter is positioned. This minimizes the number of openings 16 actually obstructed, even if some openings are obstructed in one circumferential portion of the catheter, because the twisting relationship of the lumens provides openings in other circumferential portions of the catheter that are not obstructed.

Figure 2A:
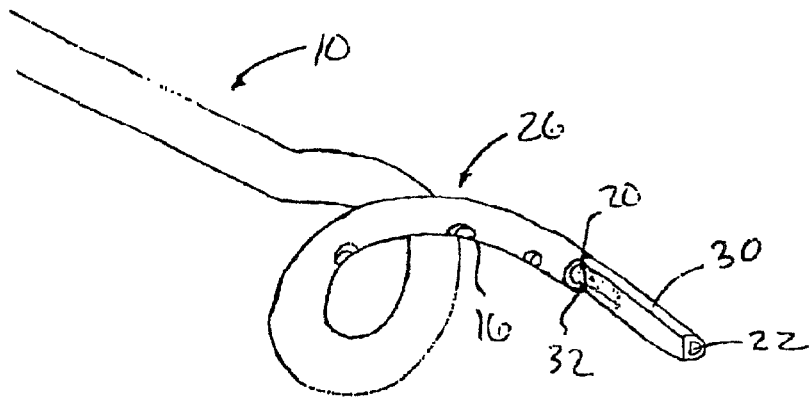
FIG. 2A shows a perspective view of an exemplary double lumen catheter having a corkscrew pattern with a relatively wide pitch.
Figure 2B:
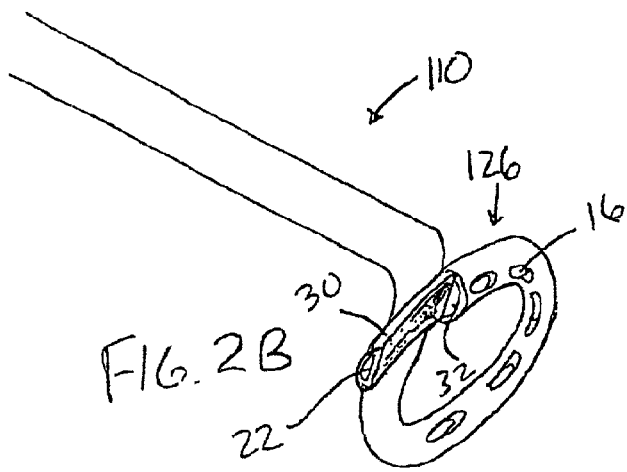
FIG. 2B shows a perspective view of an exemplary double lumen catheter having a corkscrew pattern with a relatively narrow pitch.

To further minimize potential obstruction of the openings, at least a distal portion 26 of catheter 10 (or a distal portion 126 of catheter 110) may be spirally formed into a corkscrew pattern defining a corkscrew-patterned portion, as shown in FIGS. 2A and 2B, respectively. Corkscrew patterned portion 26 shown in FIG. 2A has a relatively wide pitch, whereas the corkscrew-patterned portion 126 of catheter 110 has a relatively narrower pitch. The "pitch" as referred to herein refers to the unit length over which the corkscrew makes a full turn, a full turn being visible in an end view as completing a full circle. Although shown in FIGS. 2A and 2B having made approximately a single turn, catheters of the present invention may comprise a corkscrew pattern that makes less than or more than a full turn.

The end of the catheter of the present invention may comprise a design as shown in FIGS. 2A and 2B, where lumen 22 extends axially beyond open end 32 of lumen 20 in an extended end portion 30. Such an extended end portion may typically extend beyond lumen 20 by about 1-2 cm, and generally no more than about 3 cm. Any amount of extension may be present, however. Such a design is typically used in hemodialysis where lumen 20 is an intake lumen and lumen 22 is a discharge lumen, so that the discharge of cleansed blood may be directed downstream of openings 16 through extended end portion 30. This axial extension of the discharge lumen prevents recirculation of the discharged blood back through the intake openings 16. The extended end portion 30 may further be configured to direct the discharge in a particular location. For example, hemodialysis catheters are typically positioned above in or adjacent to the right atrium of the heart so that the discharged, cleansed blood may be discharged into the right atrium.

The catheter of the present invention is not limited to any particular end design, however, and accordingly, the end of the catheter may comprise an end perpendicular to axis A of the catheter where there is no axial offset between the end of lumens 20 and 22. The end may also be cut on a bias relative to axis A. Furthermore, the extended end portion 30 shown in FIGS. 2A and 2B is not limited to catheters with corkscrew-patterned portions, but also may be provided at the end of catheters having multi-helical twisted configurations of this invention, without a corkscrew-patterned end. Furthermore, catheters with a corkscrew patterned end portion may terminate with the extended end portion 30 of the catheter pointed axially as shown in FIG. 2A, pointed circumferentially (not shown), or pointed tangentially as shown in FIG. 2B. Furthermore, the axially, circumferentially, or tangentially pointed end portion 30 may be pointed in any direction desired to direct the discharged fluid toward a desired location, such as toward the right atrium, as discussed above.

Figure 3A:
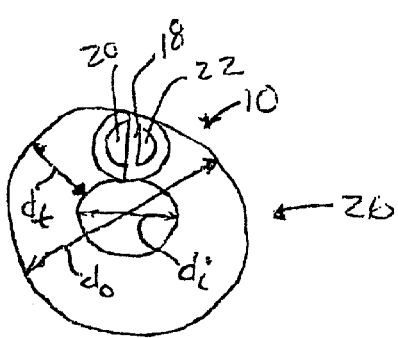
FIG. 3A shows an end view of the corkscrew pattern of FIG. 2A.

An end view of corkscrew-patterned portion 26, shown in FIG. 3A, illustrates that a corkscrew pattern inherently comprises an outer diameter $d_o$ and an inner diameter $d_i$. In one embodiment, the plurality of openings 16 may all face away from the corkscrew pattern outer diameter so that none of the openings are obstructed by contact with the body lumen. By "face away from the outer diameter" it is meant that none of the openings are located on the portion of the catheter that defines the corkscrew pattern outer diameter $d_o$. The plurality of openings may be formed in any pattern, however, including a helical pattern.

Figure 3B:
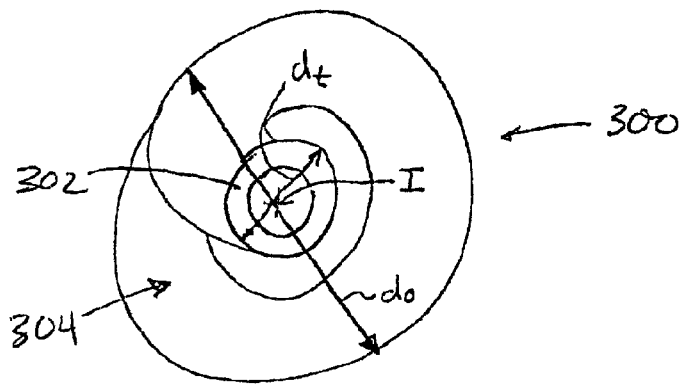
FIG. 3B shows an end view of an exemplary single lumen composite catheter comprising a corkscrew pattern.

Although discussed primarily herein with respect to multi-lumen catheters, the various embodiments of this invention are also applicable to single lumen catheters. Referring now to FIG. 3B, there is shown a single lumen catheter 300 having a corkscrew pattern, wherein open end 302 is positioned centrally inside the space 304 defined by the corkscrew pattern outer diameter $d_o$. By "positioned centrally" it means that tube diameter $d_t$ of open end 302 lies completely inside space 304 without touching outer diameter $d_o$. Although shown with the central axis I of catheter 300 coaxial with diameter $d_o$, the open end may still be considered "positioned centrally" as defined herein, even if central axis I is not coaxial with diameter $d_o$. Thus, outer diameter $d_o$ of the corkscrew pattern serves as a spacer to keep the lumen wall away from the open end.

Figure 6A:
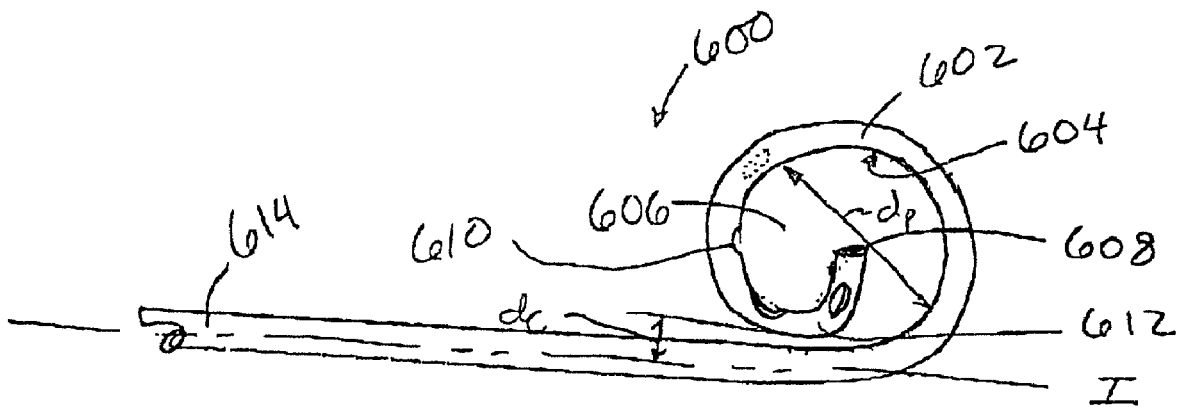
FIG. 6A shows an exemplary catheter embodiment having an inwardly spiraling portion at its distal end.

Other structural deformations in the catheter tip may similarly be used for keeping the lumen wall away from the open end. For example, as shown in FIG. 6A, catheter 600 may have an inwardly spiraling portion 602 having an inner periphery 604 with a diameter $d_p$ that defines open area 606. Open end 608 of catheter 600 may be positioned within the open area 606 so that the periphery 604 of inwardly spiraling portion 602 serves as the spacer to keep the lumen wall away from the open end. Catheter 600 may be a single lumen catheter, as shown, or a multi-lumen catheter, such as a dual lumen catheter. Catheter 600 may also have openings 610 in the sidewall. Where such openings are present, the openings may be positioned so that they face into open area 606 so as not to be obstructed by the lumen wall.

Although shown in FIG. 6A with the bottom 612 of the inwardly spiraling portion curl spaced a distance $d_c$, above axis I which runs through straight section 614 of catheter 600, the bottom of the curl may be parallel to the straight section ($d_c=0$) or may be spaced below the straight section.

Figure 6B:
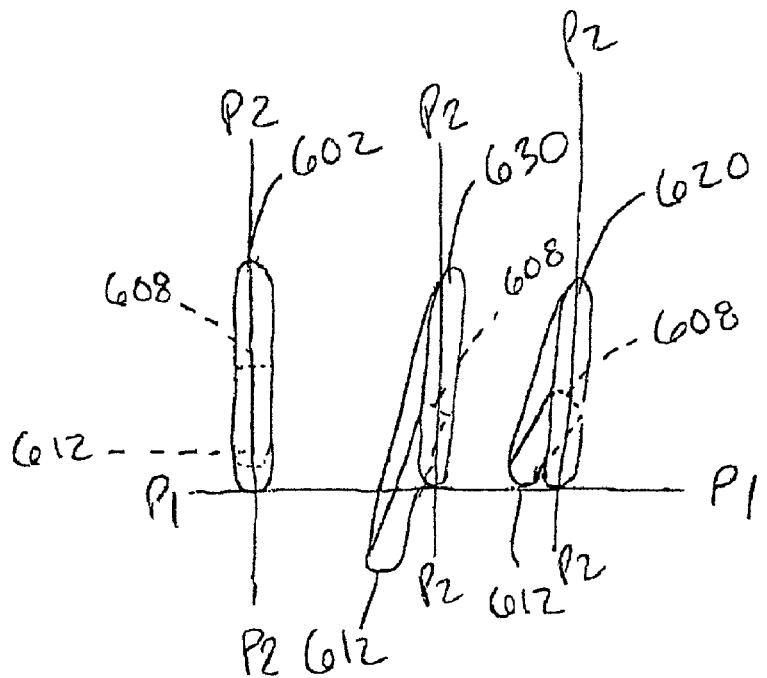
FIG. 6B shows an end view of the catheter embodiment of 6A along with two other exemplary catheter embodiments.

As used herein, the relative terms "bottom," "above," and "below" relate to the orientation on the page of the illustration provided as FIG. 6A. In other words, as shown from an end view in FIG. 6B, an inwardly spiraling portion may generally be considered a curl that lies at least partially within plane P2 perpendicular to plane P1 tangential to the lower surface of straight section 614 and parallel with axis I, the inwardly spiraling portion curling away from plane P1. In one embodiment 602, shown in FIG. 6A and as the leftmost embodiment in FIG. 6B, the curl of the inwardly spiraling portion may terminate without crossing or touching the plane P1. In another embodiment 620, the curl of the inwardly spiraling portion may come full circle with some portion coming to rest on plane P1 parallel to the straight portion 614. In yet another embodiment 630, the curl may cross plane P1. Although shown with a curl of somewhat greater than 360 degrees (wherein a 360 degree curl defines approximately a full circle), the inwardly spiraling portion may also curl less than 360 degrees or more than 360 degrees.

As noted above, although not limited to any particular catheter diameter, the tube diameter $d_t$ is typically 6-20 french (approximately 0.2-0.7 centimeters, more precisely 0.203-0.677 centimeters). Although not limited to any particular diameter, the corkscrew pattern outer diameter $d_o$ may be in the range of about 1-5 centimeters, with acceptable values being dependent upon the geometry of the body lumen into which the catheter is to be positioned.

Figure 4A:
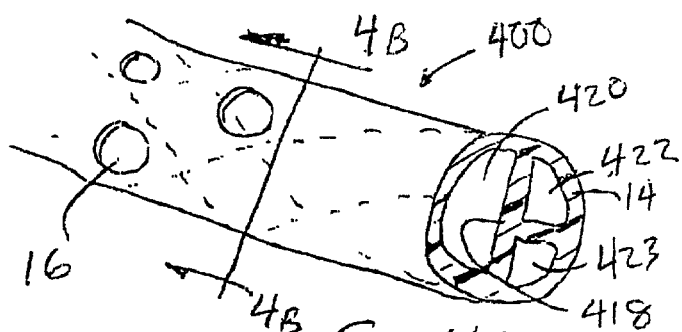
FIG. 4A shows a perspective view of an exemplary multi-lumen catheter of the present invention in partial cross-section.
Figure 4B:
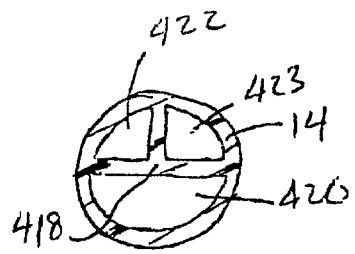
FIG. 4B shows a cross-sectional illustration of the catheter of FIG. 4A taken across line 4B-4B.

Although described above with respect to an embodiment having both the corkscrew pattern and the first lumen and second lumen forming a double helix, each of these features may be provided alone. For example, a single lumen catheter without a multi-helical relationship between or among the lumens may have an end shaped in a corkscrew pattern. Furthermore, the multi-helical twisting relationship between multiple lumens is not limited only to a double lumen design, but may be provided in a design with more than two lumens, as shown in FIGS. 4A and 4B. As shown in FIGS. 4A and 4B, catheter 400 has a first D-shaped lumen 420 and two pie-shaped lumens 422 and 423 that are formed by septum 418. Openings 16 in sidewall 14 are provided for both lumens 422 and 423. Such a design may or may not have a corkscrew-shaped end.

Figure 5:
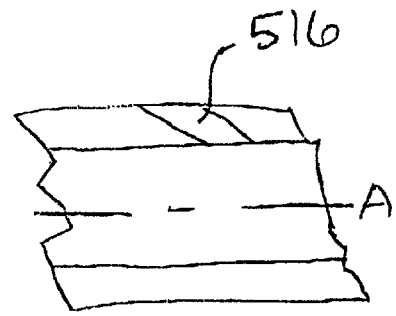
FIG. 5 shows an exemplary catheter embodiment having sidewall openings with an angled orientation.

The plurality of openings 16 may be radially formed in the sidewalls as shown in FIG. 1A (i.e., having an angle α of 90° of the central axis of the opening relative to the plane formed by the septum 18), or may comprise openings 516 that are angled (i.e., other than 90°) relative to axis A, as shown in FIG. 5. Catheter may be a perfusion catheter, such as a dialysis catheter, or any type of catheter known in the art. The catheter may be formed of any material known in the art for formation of catheters, such as flexible polymers including but not limited to polyvinylchloride (PVC), polyethylene, polypropylene, polyurethane, nylon, and thermoplastic elastomers such as PEBAX® polyether block amide, manufactured by Atofina, metal, such as nitinol or stainless steel, or a combination or composite thereof. The catheter may comprise a braided architecture, such as formed by braiding a plurality of fibers or filaments together. The filaments may comprise, for example, metal wire such as but not limited to stainless steel or nitinol, glass fibers, or carbon fibers. By "composite" it is meant that the catheter may comprise layers of different materials, or longitudinal sections of different materials. For example, one catheter embodiment may comprise a first layer of braided nitinol wire covered by a layer of polyethylene. Another catheter embodiment may comprise a relatively stiffer first longitudinal section comprising metal abutting with one or more relatively more flexible second longitudinal sections comprising a thermoplastic elastomer.

The catheters of the present invention may be manufactured by any number of methods. One method may be to injection mold the end portion of the catheter having the double-helix and/or corkscrew shape, and attach the injection-molded tip to the end of a catheter, such as a standard double-lumen catheter.

Another manufacturing method may be to first form the standard catheter, such as a double- or multi-lumen catheter, and then remold the end portion to have the desired shape. The remolding step may comprise heating the end portion to a sufficient temperature above the plastic transition temperature to allow deformation of the catheter end into the desired configuration, after which the remolded portion of the catheter cools in the desired configuration. A mandrel may be used for remolding the catheter. For example, for a double-lumen catheter, a mandrel that fits into one of the two lumens and having the desired helical relationship may be threaded into one of the catheter lumens. A second mandrel may then be fitted into the other of the two lumens, if desired, although a single mandrel may be sufficient. While one or more mandrels are preferred for producing the multi-helix configuration, a corkscrew configuration may be created by placing the catheter inside an appropriately shaped tube.

Multi-lumen catheters comprising the multi-helical design may also be fabricated during the catheter extrusion step. For example, a rotating insert in the extrusion tooling may create a catheter having the mutli-helix along its entire length. Another method comprises extruding the catheter and septum with no twist and then twisting the catheter as it exits the extruder to create the multi-helix design. Although several exemplary manufacturing methods have been provided herein, the invention is not limited to any particular method.

The catheters of the present invention may be introduced into the body by any method known in the art, including by percutaneous methods over a guidewire or with an introducer, and may include introduction through a surgically implanted access port. In a method for providing hemodialysis, a multi-lumen catheter of the present invention is first introduced into a body lumen. Then, blood from the body lumen is drawn through the openings and into the first catheter. After the blood is cleansed in a known way by hemodialysis, it is returned through the second catheter lumen and into the body lumen.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

What is claimed:

1. A catheter having a distal end and a proximal end and comprising an elongated tube having an interior defined by a sidewall and having one or more openings disposed at the proximal end and the distal end as well as a plurality of openings in the sidewall, a septum that divides the interior into at least a first lumen and a second lumen having a distalmost portion, and at least a portion of the catheter spirally formed into a corkscrew pattern to define a corkscrew-patterned portion having at least two lumens, wherein said first lumen extends distally beyond said distalmost portion of said second lumen and at least one of said openings is coincident with the corkscrew-patterned portion.

2. The catheter of claim 1, wherein the corkscrew pattern comprises an outer diameter ($d_o$) and the at least one of said sidewall openings is positioned facing away from the outer diameter.

3. The catheter of claim 1, wherein the tube has a tube diameter ($d_t$) in a range of approximately 0.2-0.7 centimeters, and the corkscrew pattern has an outer diameter ($d_o$) in a range of approximately 1-5 centimeters.

4. The catheter of claim 1, wherein the plurality of sidewall openings are distributed in a helical pattern along the sidewall.

5. The catheter of claim 1, wherein the first lumen and the second lumen form a double helix in a portion of the catheter coincident with the one or more openings.

6. The catheter of claim 5, wherein the openings are distributed on the sidewall at an angle of 90° relative to the septum.

7. The catheter of claim 1, wherein the first lumen and the second lumen form a double helix along a portion of the catheter.

8. The catheter of claim 1, wherein the septum divides the interior into more than two lumens that form a multiple helix.

9. The catheter of claim 8, wherein the more than two lumens form a multiple helix along an entire length of the catheter.

10. The catheter of claim 1, wherein the corkscrew pattern terminates with the catheter pointed in an axial direction.

11. The catheter of claim 1, wherein the corkscrew pattern terminates with the catheter pointed circumferentially.

12. The catheter of claim 1, wherein the corkscrew pattern terminates with the catheter pointed tangentially.

13. The catheter of claim 1, wherein at least a plurality of the one or more openings are radially formed in the sidewall.

14. The catheter of claim 1, wherein the catheter has a central axis, and at least a plurality of the one or more openings are formed in the sidewalls at a non-perpendicular angle relative to the central axis.

15. The catheter of claim 1, wherein the catheter is a perfusion catheter.

16. The catheter of claim 15, wherein the catheter is a hemodialysis catheter.

17. The catheter of claim 1, wherein the catheter comprises a flexible polymer.

18. The catheter of claim 1, wherein the catheter comprises a thermoplastic elastomer.

19. The catheter of claim 1, wherein the catheter comprises a material of construction selected from the group consisting of: polyvinylchloride, polyethylene, polypropylene, polyurethane, nylon, a polyether block amide, metal, carbon fibers, glass fibers, a combination thereof, and a composite thereof.

20. The catheter of claim 1, wherein the catheter comprises at least one layer that comprises a braided architecture.

21. The catheter of claim 1, having at least one open distal end and a tube diameter ($d_t$), the corkscrew pattern defines a space comprising an outer diameter ($d_o$) greater than the tube diameter, and the open end is positioned centrally within the space.

22. The catheter of claim 1, wherein the catheter comprises a tunneling catheter.

23. The catheter of claim 1, wherein said first lumen extends distally further than the distal most part said inner parameter of said second lumen by more than about 1 centimeter.

24. The catheter of claim 1, wherein said first lumen extends distally further than the distal most part said second inner parameter of said second lumen by less than about 3 centimeters.

* * * * *